(12) United States Patent
Svenson et al.

(10) Patent No.: US 6,490,471 B2
(45) Date of Patent: Dec. 3, 2002

(54) ELECTROMAGNETICAL IMAGING AND THERAPEUTIC (EMIT) SYSTEMS

(76) Inventors: Robert H. Svenson, c/o The Carolinas Heart Institute, 1000 Blythe Blvd., Charlotte, NC (US) 29232; Serguei Y. Semenov, c/o The Carolinas Heart Institute, 1000 Blythe Blvd., Charlotte, NC (US) 29232; Vladimir Y. Baranov, c/o The Carolinas Heart Institute, 1000 Blythe Blvd., Charlotte, NC (US) 29232

( * ) Notice: Subject to any disclaimer, the term of this patent is extended or adjusted under 35 U.S.C. 154(b) by 0 days.

(21) Appl. No.: 09/917,506

(22) Filed: Jul. 27, 2001

(65) Prior Publication Data

US 2002/0065463 A1 May 30, 2002

Related U.S. Application Data

(63) Continuation of application No. 09/083,224, filed on May 22, 1998, now abandoned.
(60) Provisional application No. 60/047,604, filed on May 23, 1997.

(51) Int. Cl.[7] .................................................. A61B 5/05
(52) U.S. Cl. ........................ 600/407; 324/637; 600/430; 382/131
(58) Field of Search ................................ 600/407, 425, 600/430, 547, 2, 10; 324/637, 638, 639; 382/131

(56) References Cited

U.S. PATENT DOCUMENTS

| 5,715,819 A | * | 2/1998 | Svenson et al. | ............. 324/637 |
| 6,026,173 A | * | 2/2000 | Svenson et al. | ............. 324/637 |
| 6,332,087 B1 | * | 12/2001 | Svenson et al. | ............. 324/637 |

* cited by examiner

*Primary Examiner*—Marvin M. Lateef
*Assistant Examiner*—Eleni Mantis Mercader
(74) *Attorney, Agent, or Firm*—Fredrikson & Byron, P.A.

(57) ABSTRACT

A microwave tomographic device including a single frequency three dimensional microwave tomographic system in cooperation with a single frequency three dimensional electrical impedance capable of imaging a full scale biological object is disclosed. The device includes a code division software which cooperates with a microwave patch system to, inter alia, enable superficial imaging of biological systems. A cluster of antennas and transceivers are used to provide MWT and EIT integrated in a single 3 dimensional microwave tomographic system for examining the biological from a number of views in real-time.

1 Claim, 5 Drawing Sheets

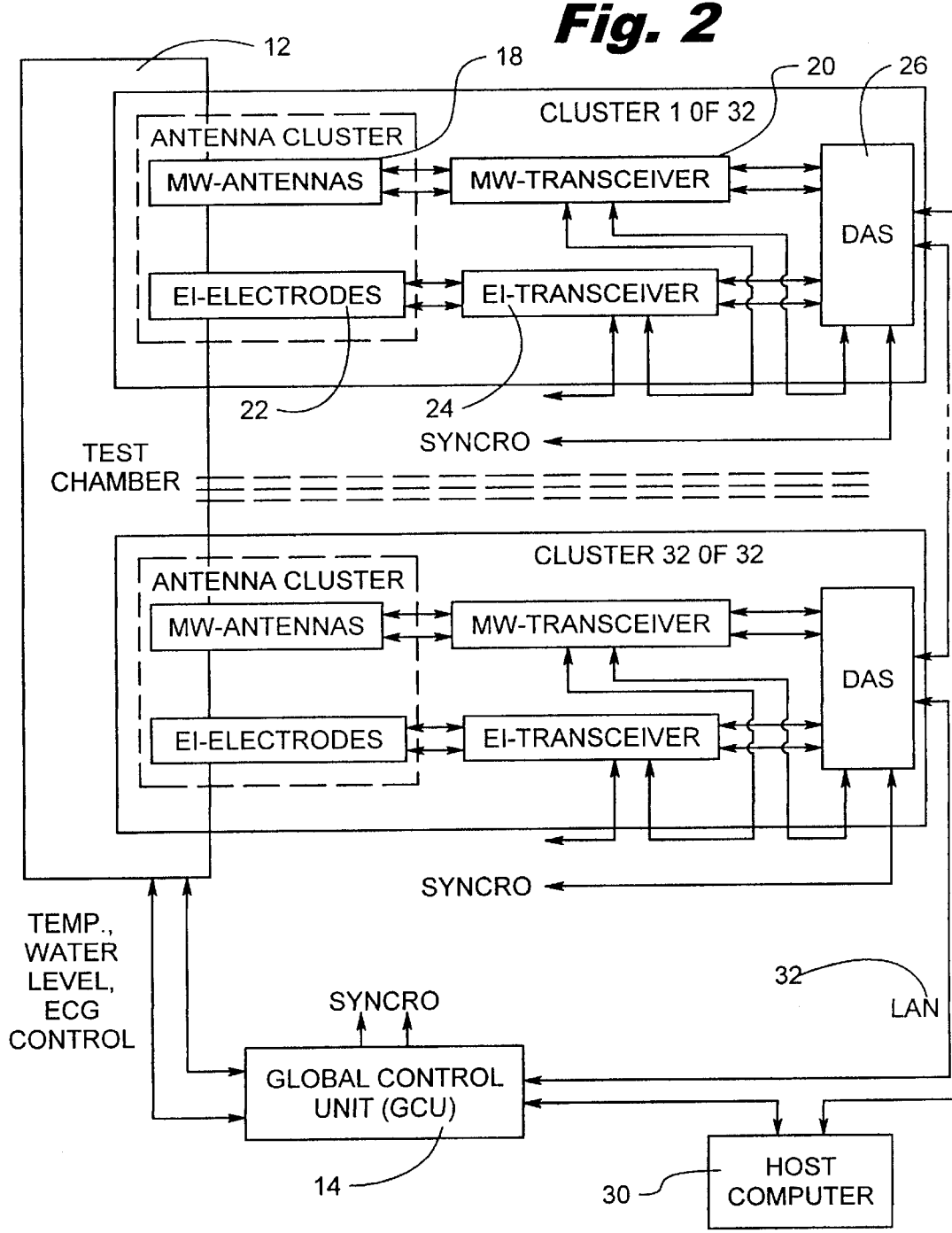

ELECTROMAGNETICAL IMAGING AND THERAPEUTIC (EMIT) SYSTEMS

This application is a continuation of co-pending, commonly assigned patent application entitled ELECTROMAGNETICAL IMAGING AND THERAPEUTIC (EMIT) SYSTEMS, Ser. No. 09/083,224 now abandoned, filed on May 22, 1998 which claims the benefit of provisional application No. 60/047,604 filed on May 23, 1997.

FIELD OF THE INVENTION

The present invention relates to EMIT systems. Specifically, the invention pertains to apparatus and method in which multi-frequency microwave in combination with preferably low frequency is structured to generate a multi-source externally focussed microwave for tissue ablation. The invention includes several versions of EMIT systems differentiated on the basis of frequency levels. Further, the invention includes a computer implemented software specifically configured and tailored to the EMIT system with a graphical and three-dimensional tomographic imaging interface.

BACKGROUND OF THE INVENTION

Microwave tomography is a relatively new technology with enormous potential for use in the medical and related industries. Specifically, the technology is becoming prominently mature and practicable for use in internal, non-invasive, real-time imaging of the physiologic properties of tissues and organs, based on tissue dielectric properties differentiation.

Prior art microwave tomographic imaging utilizes microwave radiation to image an object by detecting the effects the object had on the microwave beam after it has encountered the object. The changes effected in the reflected microwave, due to this encounter, are dependent upon the dielectric permittivity and conductivity properties of the tissues of the object being imaged. Specifically, for a given microwave frequency, the observed changes in the reflected microwave echo signify a specific signature of the imaged tissue.

Microwaves are ultra-high to super-high frequency radio waves with very short wavelengths ranging from approximately 130 centimeters down to fractions of a millimeter. Frequencies range between 0.1 Giga Hertz (GHZ) to 3000 GHZ. The microwave range which is currently used for microwave imaging of biological tissues is in the range of 0.5 to about 3 GHZ. However, other ranges of the microwave spectrum may also be used as well. The determinant in the selection of the range is that the radiation be non-ionizing to prevent destruction of tissue members or cells. Accordingly, there are biophysical parameters which should be considered when determining a compatible frequency range.

The prior art utilizes two basic categories of microwave imaging. The first category is static imaging based on forming images by determining the absolute permittivity values of the microwave radiation after its interaction with the object. The second category is dynamic imaging which is based on variations in permittivity within the object occurring at the time of incidence of the microwave radiation. The latter form of imaging is extremely useful in applications in imaging biological tissues to monitor ongoing physiological change. Both static and dynamic imaging techniques require an active imaging process whereby a microwave scanner employs moving or scanning incident radiation and detects the changes in the microwave radiation based on interaction with the object being imaged.

Using dynamic imaging, image reconstruction is based on the difference in diffracted fields recorded from several data sets taken from a body with a changing dielectric contrast. However, internal imaging within larger bodies poses resolution problems which limit the application and scope of dynamic imaging. The present invention, including the related disclosures attached herewith, provide significant advances over the prior art by integrating biophysical, computer software and microwave tomography technologies to provide a high resolution image.

SUMMARY OF THE INVENTION

The invention integrates and implements biophysical, algorithmic/computer and microwave tomography devices and method to provide a three-dimensional tomographic system. Specifically, the invention includes a new method and system for medical physiological tomography wherein a one frequency three dimensional microwave tomographic system (3D MWT) is combined with one frequency three dimensional electrical impedance tomographic system (3D EIT) capable of imaging a full scale biological object(s) such as a human torso.

Specifically, the present invention provides an internal, non-invasive, real time imaging of the physiologic properties and temporal changes of tissues and organs based on tissue dielectric properties differentiation. For example, using the invention it has been shown that the dielectric properties of the myocardium are sensitive indicators of its physiological condition, including local blood supply, ischemia and infarction. The degree of change in the myocardial dielectric properties provides adequate data for reconstruction using microwave tomography. More specifically, the invention includes an EMIT system with a number of microwave frequencies (microwave spectroscopy) and one frequency (about 0.2 MHZ) lower than the cellular membrane relaxation frequency. This frequency composition of the invention enables estimation of biophysical parameters of the tissue as cellular volume fraction, intracellular and membrane resistivities, cell membrane capacitance, tissue free and bound water content and tissue temperature. It should be noted that such information is critical not only for cardiology but also for other branches of medicine, inter alia, oncology, urology, neurology and (preliminary information) HIV studies.

Further, the present invention provides mathematical models and computer implemented algorithms for constructing heretofore unavailable quantitatively reconstructed clear structural images which depict exact distribution of dielectrical properties within an object.

Furthermore, the present invention provides a therapeutic device providing internal local overheat of the tissue by electromagnetic energy focusing.

BRIEF DESCRIPTION OF THE DRAWINGS

FIG. 2 is a schematic diagram of the major component parts of the 3 D tomographic system.

DESCRIPTION OF THE PREFERRED EMBODIMENT

Figure 1:
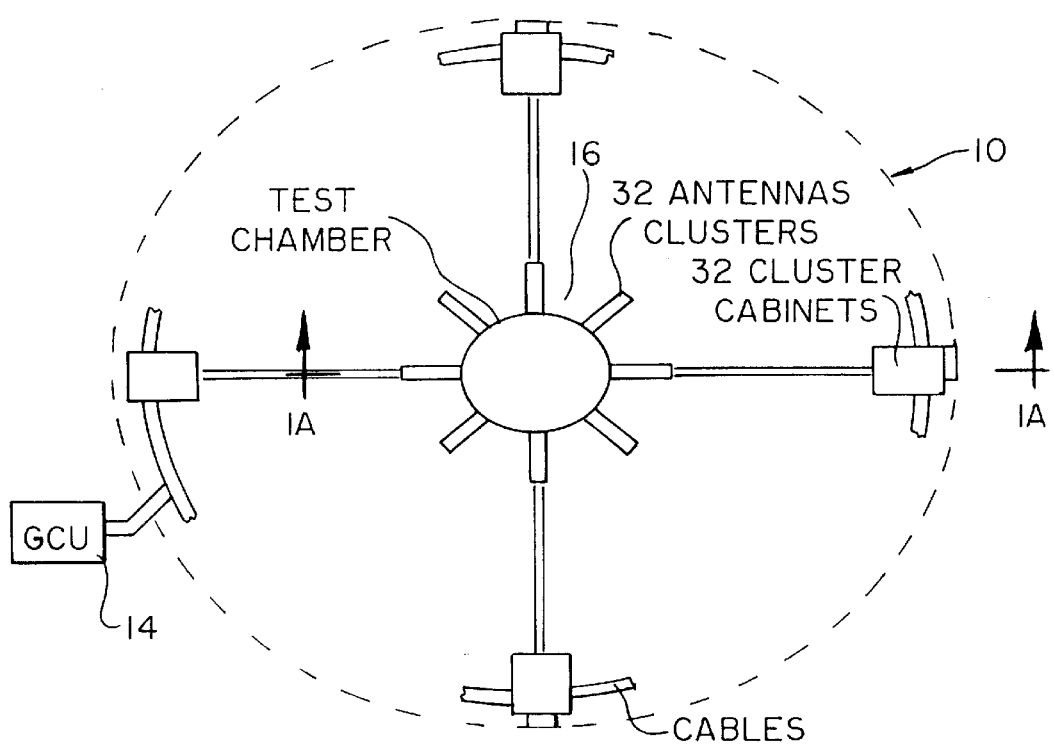
FIG. 1 is a general view of the 3 D tomographic system.
Figure 1A:
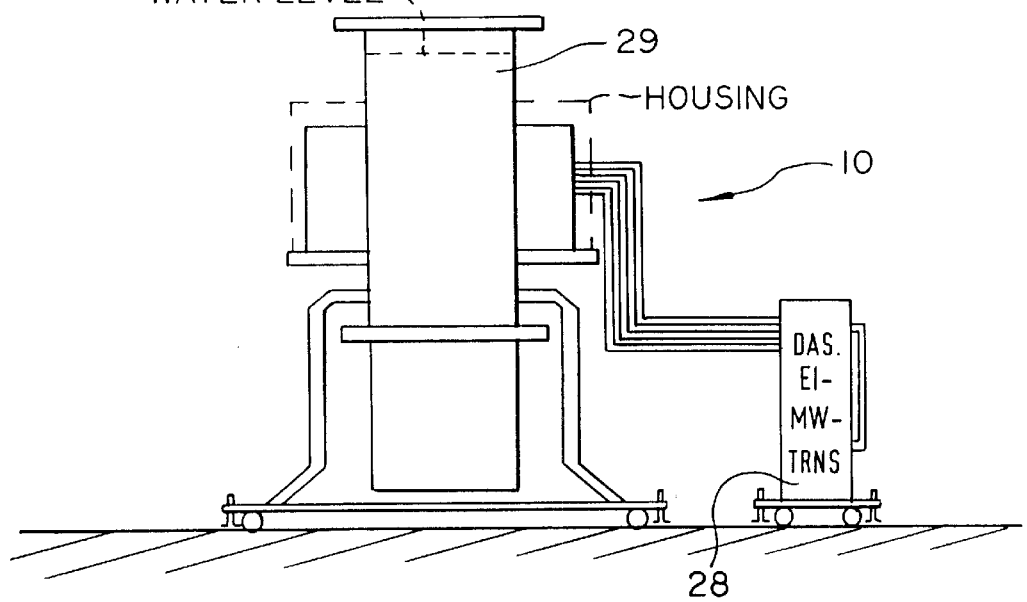

The present invention provides a three dimensional microwave tomographic system which is combined with a three dimensional electrical impedance tomographic system. Specifically, the invention includes a one frequency three dimensional microwave tomographic system combined with one frequency three dimensional electrical impedance tomographic system capable of imaging a full scale biological object(s) such as, for example, a human torso or portions thereof. The disclosures of the present invention provide both theoretical and experimental values which show some of the advantages and advances of the invention relative to the prior art currently available in medical diagnosis and therapy.

The present invention contemplates a staged approach in which a first generation EMIT system is launched with possible upgrades to a second generation system. The first generation is distinguished in that it has two systems having the following characteristics (a) Multifrequency microwave spectroscopic tomographic 0.2–6 GHZ, and (b) single microwave frequency (0.8 to 1 GHZ) with a single low frequency (200 KHZ). The second generation comprises of three systems with the following distinguishing characteristics: (a) Multifrequency microwave 0.2–6 GHZ, (b) One low frequency approximately 200 KHZ and c) multisource externally focussed microwave for tissue ablation (60° C.).

Further, the present invention provides unique algorithms and software to enable the generation of very accurate images from the EMIT systems. Specifically, the algorithms enable image reconstruction from microwave tomography. Since the linear optics approximation used in X-ray tomographic image construction is not readily adaptable to microwave tomography primarily because of electromagnetic wave propagation through biological media involving diffraction and interference phenomenon, there is a need to develop specific algorithms to solve Maxwell equations or their scalar approximation. The present invention provides algorithmic models and software programs to solve these equations and enable a reconstruction of images as needed. Details of the types of models, assumptions, limitations and related mathematical postulations are discussed in copending application Ser. No. 08/896,525, filed Jul. 4, 1997 (indicated on some documents as Ser. No. 08/896,526 filed Jul. 5, 1997), No. 60/047,604, filed May 23, 1997, and Ser. No. 08/250,762, now U.S. Pat. No. 5,715,819, assigned to the assignee of record and are incorporated herein by reference.

The present invention provides MWT and EIT integrated in a single 3 dimensional microwave tomographic system. The system enables examination of large biological objects. The device and method of the present invention provide hitherto unknown and unattainable advances and advantages in the field. Specifically, the invention enables a totally non-invasive tomographic system. Typically, the energy of "photons" in the microwave region is small enough to avoid ionization effects which are encountered in X-ray tomography. Furthermore, all tomographic systems for internal body imaging are based on the differentiation of tissue properties. For example, in X-ray tomography tissue is differentiated based on density. However, tissue density does not always depend on the tissue physiological state. Important tissue characteristics such as temperature, blood content, blood oxygenation, ischemia, infarction cannot be differentiated by X-ray tomography. As is disclosed in the copending applications, incorporated herein by reference, tissue properties can be described by means of their complex *dielectric* value $\in$' and cellular volume fraction.

Generally, the anatomical structure of an object can be easily reconstructed using traditional methods such as X-ray or NMR tomography. However, the information about physiological conditions of the tissue can not be reliably received from either or both X-ray and NMR tomography. There are significant limitations in effectively combining these tools. First, the information received in NMR technology reflects primarily a nucleus condition because it relates to resonance of nucleus spin in external field. Second, NMR requires long acquisition time for physiological imaging. Overcoming these limitations requires very high power and homogeneous magnetic fields which pose risks to patients in addition to posing operational and design related technical limitations.

The present invention provides a simultaneous examination of the object from a number of views in real-time. Referring now to FIGS. 1 and 2, a block schematic diagram of 3D tomographic system 10 is shown. The system includes test chamber 12, global control unit 14 and clusters of antennas 16. Each cluster comprises MW antennae 18, MW transceiver 20, EI electrodes 22, EI transceivers 24, DAS (data acquisition system) 26, and power source 28. Preferably the cluster is adjustably mounted on precision positioning system 29. System 10 further includes host computer 30 in data communication therewith.

An object for investigation is placed in test chamber 12, filled with solutions having different dielectric properties. Test chamber 12 includes temperature, solution level, patient ECG and other related sensors. Global control unit 14 controls system function and generates and distributes synchronous signals. Both MW antennae 18 and EI electrodes 22 are integrated into antennae clusters 16 and are used for irradiation and receiving signals. Antennae clusters 16 comprise low noise amplifiers and output stage amplifiers for MW transceivers 20 and EI transceivers 24 in addition to providing control for channel distribution network. MW transceivers 20 and EI transceivers 24 amplify, modulate and transform multiple signals. Data acquisition system 26 is used for sampling, filtering and processing of signals in cooperation with host computer 30 and LAN 32.

Figure 3:
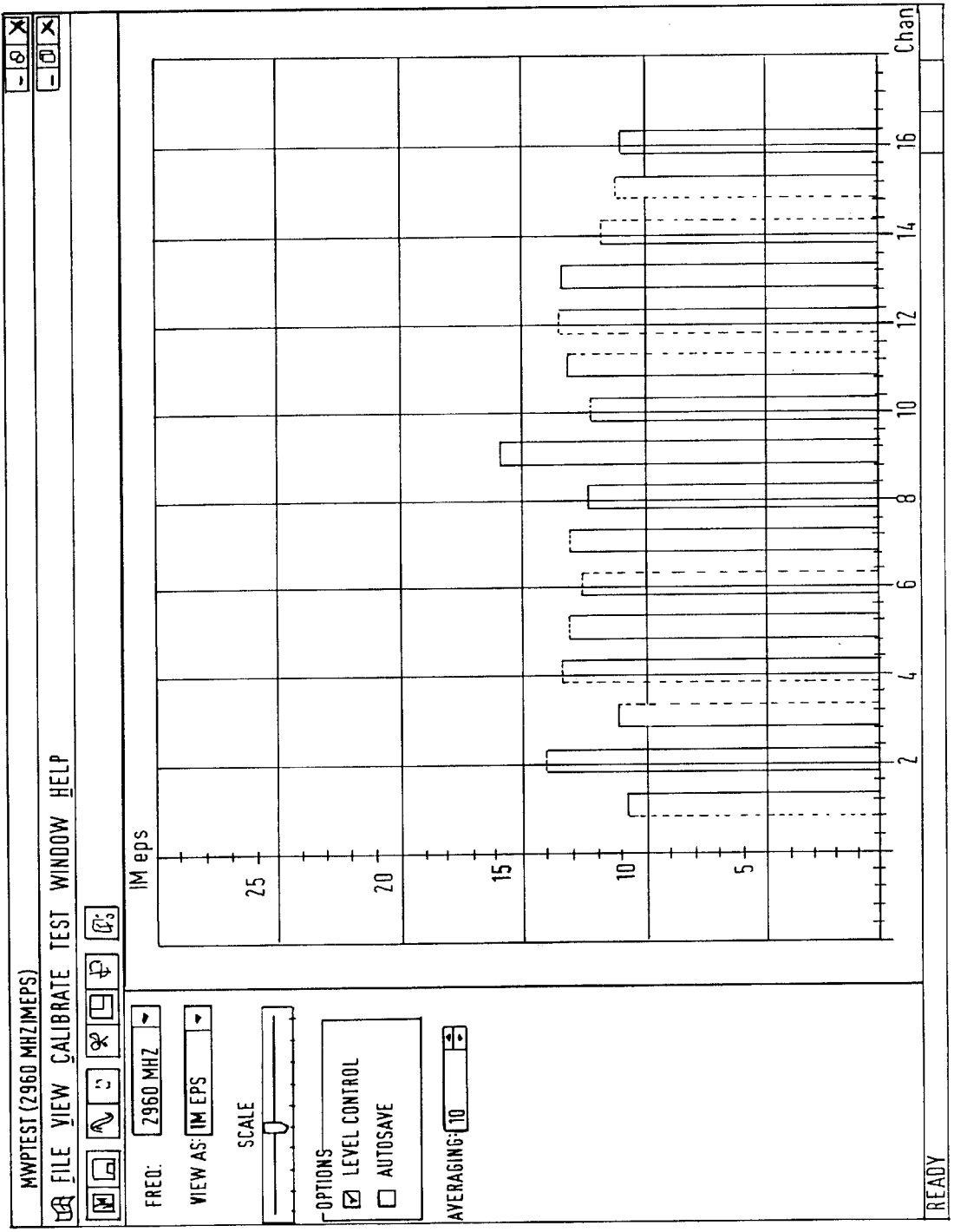
FIG. 3 is a screen display of an MW patch for a single window menu.
Figure 4:
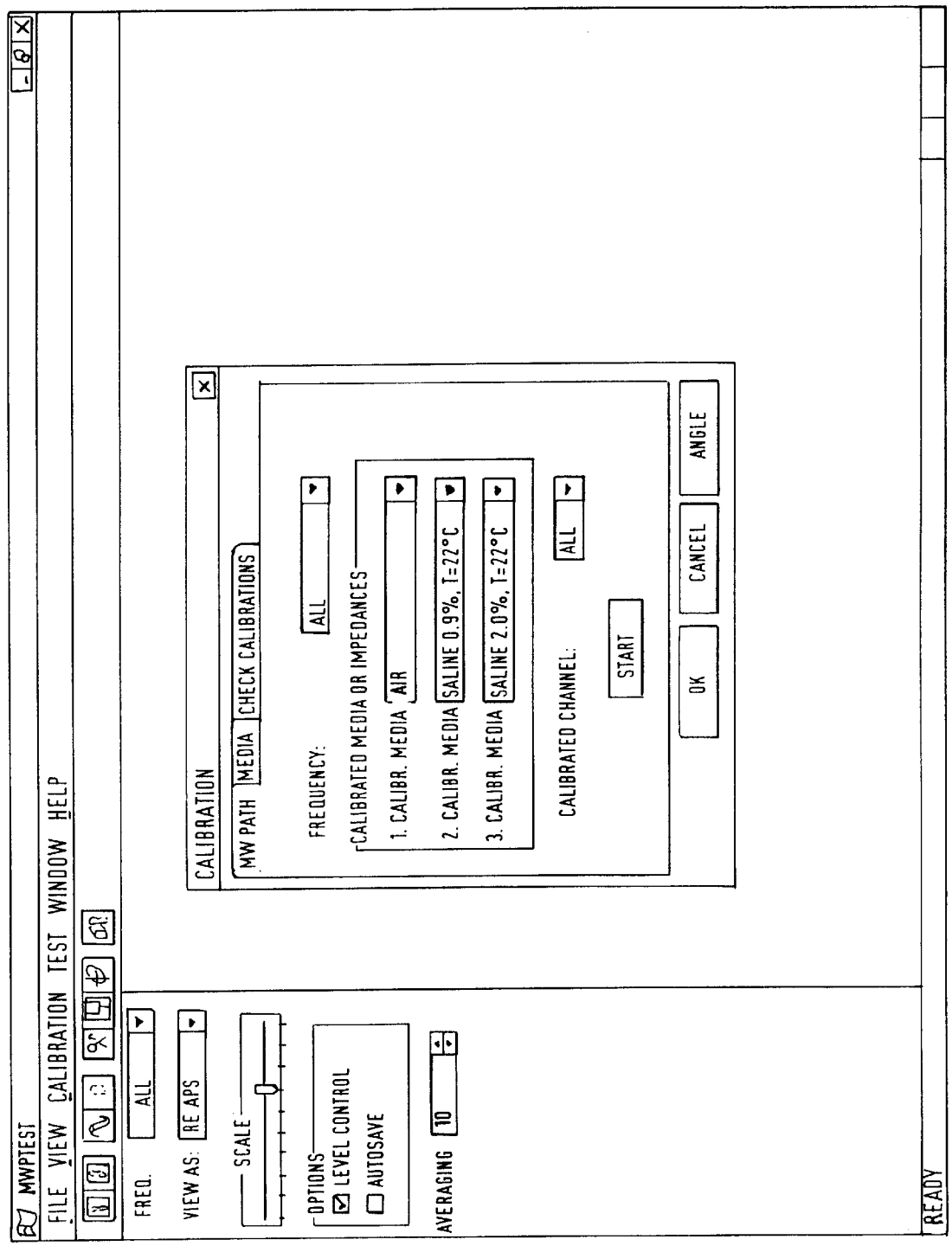
FIG. 4 is a screen display of an MW patch calibration menu.
Figure 5:
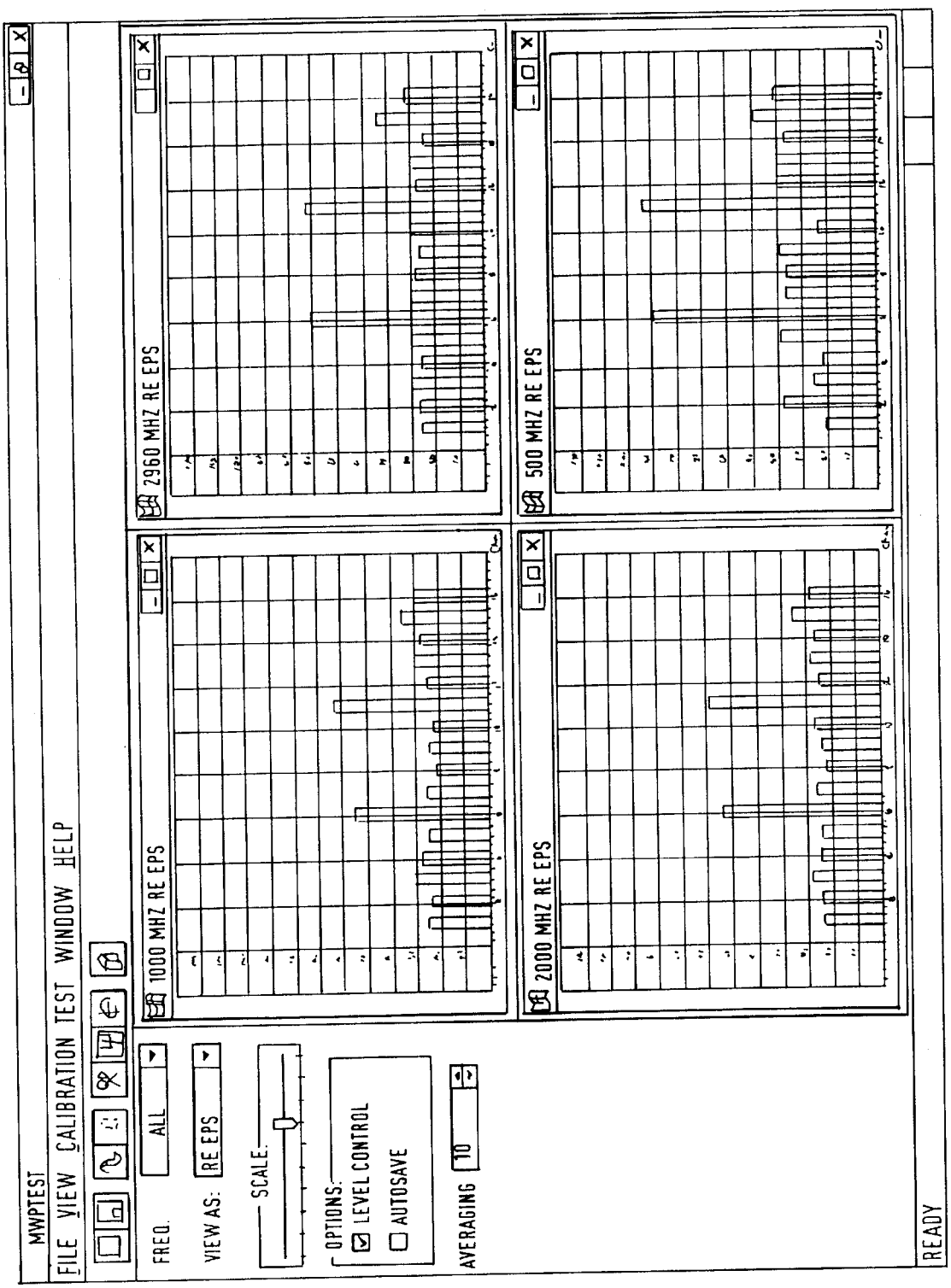
FIG. 5 is a screen display of an MW patch for a 4 window menu.

Referring now to FIGS. 3–5 a multichannel multifrequency microwave patch system is illustrated. Microwave patch system is the device for superficial microwave imaging of biological tissues. Generally, existing patch systems are limited to a single channel and are used to measure dielectric properties utilizing coaxial probe and network analyzer. These measurements are neither precise nor sufficiently refined enough to give accurate readings. In sharp contrast, the present invention provides a patch system which implements multichannel complex reflection coefficient measurements, in real time, at high accuracy levels. The patch system of the present invention includes a non-invasive in vitro measurement procedure with up to 6 switched frequencies from 0.1 GHz to 5 GHz. The system further enables real time measurements and visualization. Further, unlike prior art patch systems, the calibration does not require precision microwave equipment. Host computer 30 is preferably controlled using RS-485 interface or equivalent and a code division technique is implemented to enhance the speed of data acquisition.

Accordingly, FIG. 3 depicts a sample of a screen display of an MW patch for a single window menu. The menu bar includes file, view, calibration, test, window and help bars. Selections can also be made for various frequencies and viewing options. For example, the screen display of FIG. 3 shows IM eps at frequency of 1960 MHz spread over 16 channels.

FIG. 4 illustrates a sample of a screen display for calibration in which for a given frequency the medium/media or impedance are calibrated. The menu bar includes frequency selection options and viewing options. Calibration may be done for all, one or more than one channels.

FIG. 5 illustrates a sample of a screen display of an MW patch for 4 windows. The arrangement enables one to post various frequency readings and the respective channel readings.

As illustrated in FIGS. 1–2, 3D tomographic system 10 includes microwave generator, data acquisition system 26 including control processors. Further, active antenna array in the manner of antenna clusters 16 and precision positioning system 29 capable of moving antenna clusters 16 along preset coordinates are structured to enable selective object viewing and examination. Antenna cluster 16 can be aligned along a preset axis and is controlled by a digital signal processor to obtain 32 scattering patterns simultaneously. All transmitter antennas simultaneously irradiate an object under study with preferably vertically polarized electromagnetic waves. Simultaneous irradiation results in a superposition of electromagnetic fields in the receiver. The code division method is used for rebuilding desired scattering diagrams from the multiple signal. Data acquisition system 26 performs sampling and filtering functions and implements the code multiple signals from the receiver and to assign values of scattered field (amplitude and phase) from any antennae in antennae cluster 18.

Some of the significant advantages of the present invention include vector field measurement capabilities in cooperation with a precision positioning system. Further, code division techniques are implemented for simulation and parallel measurement. The number of receiving antennas is structured to be sufficient for high field oscillations caused by scattering due to dielectric inhomogeneities and interference with the incident field. This consideration in the structure, number and orientation of the receiving antenna is critical for an accurate measurement of the phase of scattered signal. Similarly, the number of emitters should be sufficient for accurate matrix determination during reversal of the matrix.

Accordingly, the present invention advantageously combines one frequency three dimensional microwave tomographic system with one frequency three dimensional electrical impedance tomographic system to image an object. The system is useful in physiological imaging as particularly applied to medical diagnosis and therapy.

While the preferred embodiments of the present invention have been shown and described, it will be obvious to those skilled in the art that changes, variations and modifications may be made therein without departing from the present invention in its broader aspects.

What is claimed is:

1. A code division software method implemented in a microwave tomographic device having a single frequency three dimensional microwave tomographic system in cooperation with a single frequency three dimensional electrical impedance capable of imaging a full scale biological object, the code division software comprising:

means for collecting scattering diagram data from a plurality of signals;

means for sampling and filtering; and means for assigning values, said means for collecting being a data acquisition system having said means for sampling and said means for assigning being incorporated therein to implement said code division software.

* * * * *